US00PP09847P

United States Patent [19]

Riordan et al.

[11] Patent Number: Plant 9,847

[45] Date of Patent: Apr. 1, 1997

[54] 315 BUFFALOGRASS

[75] Inventors: Terrance P. Riordan; Susan A. de Shazer Steele, both of Lincoln, Nebr.; Milton C. Engelke, Parker, Tex.; Leonard A. Wit, Jr., Bennet; Frederick P. Baxendale, Lincoln, both of Nebr.; Jeana L. F. Svoboda, Altus, Okla.; Jennifer M. Johnson-Cicalese; Edward J. Kinbacher, both of Lincoln, Nebr.

[73] Assignee: Board of Regents, University of Nebraska Lincoln

[21] Appl. No.: 442,845

[22] Filed: May 17, 1995

[51] Int. Cl.[6] ..... A01H 5/00

[52] U.S. Cl. ..... Plt./90

[58] Field of Search ..... Plt./90

[56] References Cited

U.S. PATENT DOCUMENTS

| | | | |
|---|---|---|---|
| P.P. 7,539 | 5/1991 | Engelke et al. | Plt./90 |
| P.P. 8,475 | 11/1993 | Riordan et al. | Plt./90 |
| P.P. 9,208 | 7/1995 | Mancino | Plt./90 |

*Primary Examiner*—James R. Feyrer
*Attorney, Agent, or Firm*—Suiter & Associates PC

[57] ABSTRACT

A vegetatively reproduced buffalograss cultivar, named 315 Buffalograss, is distinguished by its excellent dark green color, high density, low growth habit, drought resistance, heat and cold tolerance, wear tolerance, low maintenance requirements and slow rate of establishment.

1 Drawing Sheet

BACKGROUND

Buffalograss, *Buchloë dactyloides* (Nutt) Engelm., is a perennial, low-growing, drought tolerant species that spreads by profusely branching stolons and thrives under semi-arid conditions even under heavy grazing pressure. Buffalograss is the only turfgrass species which can withstand all combinations of cold, heat and drought stress and still maintain an attractive turf under low to medium maintenance levels.

Native to an area extending from Central Mexico to Southern Canada which receives an annual precipitation of 38 to 63 cm. Buffalogreass has a secondary range of adaptation along the perimeter of its primary range, in which it can displace less well-adapted grasses given favorable conditions of soil, altitude (<2000 m) and competition. Buffalograss cannot endure competition of taller species under climatic conditions that favor these species.

Following the drought of the 1930's, buffalograss reestablished itself as a grass of great agricultural and conservation importance, having survived the combined effects of dust, drought, plowing and overgrazing. Its aggressive stoloniferous growth habit and dense sod forming capabilities proved very effective at binding soil to prevent wind and water erosion. Buffalograss sod also exhibits high water holding capacities, usually 57 to 60%.

Buffalograss has emerged as an excellent drought-resistant native species with an evapotranspiration rate of less than 6 mm per day, less than any other commonly used warm or cool season turfgrass. Some of the characteristics responsible for this drought resistance are its finely branched root system, aggressive low growing aerial parts and the ability of leaf blades to limit transportation by tightly rolling during drought stress. Buffalograss is able to to dormant sooner than other grasses and revives quickly when the drought stress is removed. In comparison with other grasses, at reduced mowing heights buffalograss shows increased survival, growth rate and weed resistance. These characteristics all make buffalograss a potentially outstanding turfgrass with minimal negative effects on the environment.

Buffalograss can be established by two methods: vegetative propagation or seeding. Traditionally, vegetative propagation of plugs or sod pieces has been employed because of difficulties in seed production and seed establishment.

Recent developments in equipment such as automated pluggers and "big roll" sod handlers have further enhanced the appeal of vegetative propagation. Improvements have also been made in seed production and seed treatment.

Buffalograss use is increasing, especially in low maintenance areas. It has been successfully established on highway shoulders and right-of-ways, airfield runways, cemeteries, parks, golf courses and other athletic field areas. Because of environmental concerns, water shorages and changes in personal priorities, buffalograss now has tremendous potential as a turfgrass. Efforts in breeding and development of buffalograss are relatively new, and the emphasis of this work has been on developing turf-type cultivars which maintain the ecological efficiency of the species, yet have a lower growth habit, increased rate of spread, improved color, extended growing season, increased density, and good recuperative potential.

SUMMARY OF THE INVENTION

NE 84-315 buffalograss is distinguished from other commercially available cultivars in being a vegetatively propagated female plant with a darker green color and lower growth habit than "Prairie" or "609" buffalograsses. NE 84-315 has better overall quality, appearance, density and uniformity than seeded varieties. It has a slower establishment rate than "Prairie" or "609" and is adapted to both Northern and Southern portions of the United States. NE 84-315 provides an attractive, wear tolerant turf which requires less water, fertilizer and mowing than other turfgrass species. These characteristics, along with on-site testing, have shown that NE 84-315 is well adapted to golf course roughs, home lawns, and institutional areas requiring a reduced management level.

BRIEF DESCRIPTION OF THE PHOTOGRAPHS

DETAILED DESCRIPTION OF THE PLANT

Figure 1:
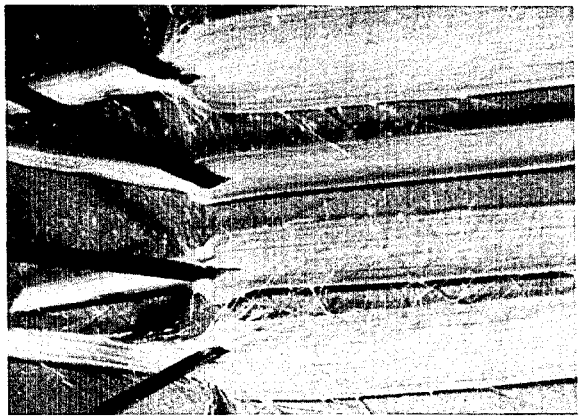
FIG. 1 is a photograph of NE 84-315 in Yuma, Ariz. under drought conditions.
Figure 2:
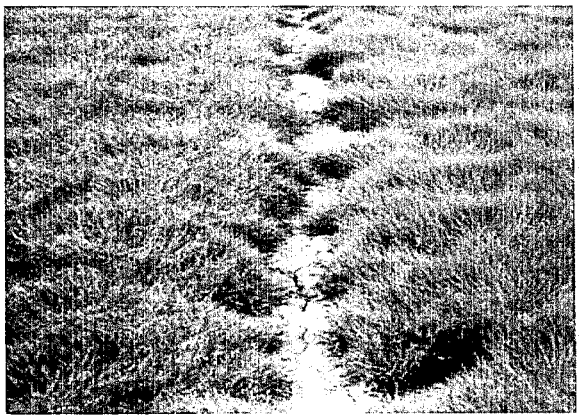
FIG. 2 is a photograph of NE 85-378 buffalograss (left) and NE 84-315 (right).
Figure 3:
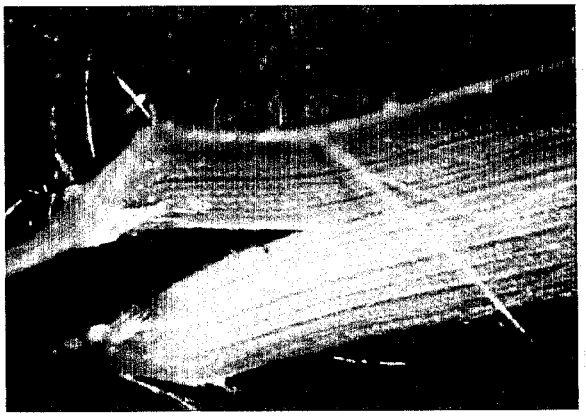
FIG. 3 is a photograph of NE 84-315 in Tucson, Ariz.

NE 84-315 is derived from a plant designated TAES 1303 which was originally collected in 1980 from a native buffalograss stand in Fort Collins, Colo. TAES 1303 and 149 other native accessions were planted in an open-pollinated hybridization nursery. Seed was individually harvested from these accessions, germinated and planted out in a new nursery. From this progeny population, a superior female offspring of TAES 1303 was identified and designated TAES 1303.1. After a few years growth of this nursery, a single plant was selected in the vicinity of the TAES 1303.1 clone and named NE 84-315. Thus NE 84-315 may be TAES 1303.1 itself or a volunteer seedling of TAES 1303.1. This selection was evaluated along with several thousand others at the John Seaton Anderson Turfgrass Research Facility near Mead, Neb. The original parental and progeny lines TAES 1303 and TAES 1303.1 were not maintained after Texas A&M discontinued its buffalograss breeding project in 1984.

The growth characteristics of buffalograss can be used to distinguish one cultivar from others. In a greenhouse study, the length of internode 1 of NE 84-315 was less than that of "Texoka" and "609", while the internode width was comparable to these genotypes (Table 1). The leaf blade length of NE 84-315 was less than "Texoka" and greater than "609", and leaf widths were the same for each genotype (Tables 2 and 3). Measurements of the spikelet length indicate that NE 84-315 had a much shorter spikelet than the standard "Texoka" and was comparable to "609" (Table 4). In a Nebraska field trial, NE 84-315 produced more inflorescences than "Texoka" and had a more dense canopy than "Texoka" or "609" (Table 5). NE 84-315 has significantly more leaf pubescence than "609" or "Prairie" (Table 6).

NE 84-315 has been evaluated at several locations throughout the United States. In most tests NE 84-315 was compared to "Texoka", a commercial standard "Prairie", a new release from Texas A&M; "609", a new release from the University of Nebraska; and other experimentals which are being considered for release. In these evaluations NE 84-315 was also compared with AZ-143, a plant of equivalent ploidy. These comparisons are described in U.S. Plant Pat. No. 9,208 which is incorporated herein by reference.

In the Southern location of Texas A&M-Dallas, NE 84-315 had slower establishment than "609" and "Prairie", both well adapted to the deep South, and "Texoka", adapted to the Northern United States (Table 7). In Colorado, NE 84 315 had comparable establishment to "609" and "Texoka" (Table 8). The Southern Illinois study indicated that "315" had better establishment than "609" (Table 9). NE 84-315 was also less sensitive to an application of the herbicide Principle® than was "609" (Table 9). Stolon length measurements at Texas A&M-Dallas showed that NE 84-315 produced fewer and shorter stolons than "609" and "Prairie" (Table 10). In Nebraska, NE 84-315 exhibited excellent, but generally slower, establishment in all plantings, including increases of material for plant breeders' nurseries and experimental plot areas (Table 11). NE 84-315 has established well in tests under sod farm conditions in Texas, Missouri and Nebraska. However, NE 84-315 does not produce as strong a sod as either "609" or "Pairie".

Buffalograss is a warm-season species that will greenup later and go dormant earlier than cool-season species such as Kentucky bluegrass. Although this characteristic may be disadvantageous in the Northern part of the United States, buffalograss may have a longer growing season than other warm-season turfgrasses in the South. Spring greenup has been evaluated at both the University of Nebraska and at Texas A&M-Dallas. NE 84-315 had a spring greenup rate faster than "Texoka" and "609" in Nebraska (Table 12). In Texas, NE 84-315 was slightly slower to green up initially, but later it was greener than all other genotypes (Table 13). In a Mead, Nebraska trial, NE 84-315 went dormant earlier in the Fall than "609" and "Texoka" (Table 14). Although a later Fall dormancy in the North would be desirable, it is possible that the early Fall dormancy of NE 84-315 results in greater cold hardiness than "609" and "Prairie".

Turfgrass color is an important component of turfgrass quality. NE 84-315 generally has a darker, more attractive color than commercial standards "609", "Texoka" and "Prairie". In Texas, NE 84-315 was dark green early in the Summer, but lost this color as the grass became dormant (Table 15). In Nebraska, NE 84-315 had a darker color than "609" and "Texoka" in the Spring, and for the yearly average (Table 16).

Turfgrass quality is a rating used to indicate the aesthetic value of a turf cultivar. This characteristic is very important in buffalograss because its turf potential has been overlooked in the past. NE 84-315 had above average or average turfgrass quality during the growing season at each location in the South (Tables 17, 18 and 19). At the University of Nebraska, NE 84-315 had turfgrass quality ratings superior to those of "Texoka" and "609" (Table 20).

Reduced water use and drought stress avoidance are important characteristics of drought resistance in buffalograss, contributing to its lower maintenance cost. NE 84-315 has been shown to have moderate heat and drought stress tolerance at Dallas, Tex. (Table 21). Frost is another stress that NE 84-315 has been shown to tolerate (Table 22).

Density is an important component of turfgrass quality. In studies at the University of Nebraska, NE 84-315 had turfgrass density ratings better than "Texoka" and "609" during the Summer (Table 23). The height of NE 84-315 is significantly less than that of "Texoka" in evaluations done in the University of Nebraska (Table 24).

The Variety

Origin: Cultivar of a single superior female plant (TAES 1303.1) selected from the progeny of a plant (TRES 1303) collected in Fort Collins, Colo., and open-pollinated by a collection of native accessions from the Great Plains. NE 84-315 may be TAES 1303.1 itself or a volunteer seedling of TAES 1301.1.

Classification:

*Botanic.*—*Buchloë* dactyloides (Nutt.) Engelm.

Chromosome number: 60 chromosomes (hexaploid).

Form: Monocot Gramineae.

Growth habit: A perennial female plant with a stoloniferous growth habit allowing vegetative propagation. It will spread slowly under non-competitive conditions favorable to stolon production. It has a very fibrous root system with a depth of 100 to 150 cm. It will produce a dense, fine textured turf with excellent dark green color throughout most of the growing season.

Establishment rate:

*Plugs.*—12 to 14 weeks with irrigation.

*Sod.*—1 to 2 weeks.

*Sprigs.*—Not recommended.

Regions of adaptation: North/South from the Canadian border to the Mexican border and East/West from Missouri to California. The exact geographic region of adaptation is currently under investigation.

Dormancy and Regreening:

*Winter hardiness.*—Winter hardy from Mexico to Canada.

*Dormancy.*—Earlier than Kentucky blue grass, "609" and "Prairie" buffalograsses (approximately October 1 in Nebraska).

*Spring greenup.*—Later than Kentucky bluegrass and earlier than "609" and "Prairie" buffalograsses (approximately May 1 in Nebraska).

Blade:

*Shape.*—Long, slender.

*Length (mature).*—14.6 cm.

*Width.*—1.2–1.3 mm.

*Pubescence.*—Heavy, having an average of 6.5 axial and 4.9 adaxial trichomes per square millimeter compared to other buffalograsses such as "Prairie" and "609" with an average of 0 to 0.3 trichomes per square millimeter.

Mature plant height: 15 cm.

Above canopy stolon production: Minimal compared to Prairie.

Internode length: 4–4.5 cm (internode 1).

Internode width: 0.8 mm.

Node pigmentation: green;

Stolon color:

*Midsummer.*—Typically green (138B).

*Winter.*—Brown (165C).

Leaf color:

*Midsummer.*—Bluegreen (141C) to dark green (141B).

*Winter.*—Brown (165C). Royal Horticultural Society Colour Chart Designations.

Soil adaptation:

*Heavy soils.*—Silty clay loam preferred, slightly acid to alkaline pH.

Female inflorescence: Present, heavy at certain portions of the growing season.

Male inflorescence: Absent.

COMPARATIVE DATA

The following tables provide data comparisons of selected characteristics of "315" compared to "609", "Texoka", and in some cases "Prairie".

TABLE 1

Internode Length and Width: University of Nebraska Greenhouse Winter 1988

| | Internode Length (cm)[1] | | Internode Width (mm)[1] | |
|---|---|---|---|---|
| | Internode 1 | Internode 2 | Internode 1 | Internode 2 |
| NE 84-315 | 4.2 ± 0.7 | 4.3 ± 0.9 | 0.8 ± 0.1 | 0.8 ± 0.1 |
| 609 | 7.2 ± 3.0 | 2.0 ± 2.5 | 0.9 ± 0.1 | 0.9 ± 0.1 |
| Texoka | 6.6 ± 1.7 | 6.2 ± 0.4 | 0.8 ± 0.1 | 0.9 ± 0.1 |

[1]Average of 10 measurements.

TABLE 2

Leaf Blade Length Characteristics: University of Nebraska Greenhouse Winter 1988

| | Leaf Blade Length (cm)[1] | | | |
|---|---|---|---|---|
| | Shoot 1 | | Shoot 2 | |
| | Leaf 1 | Leaf 2 | Leaf 1 | Leaf 2 |
| NE 84-315 | 4.0 ± 1.2 | 3.1 ± 1.2 | 3.7 ± 1.6 | 2.9 ± 1.2 |
| 609 | 3.5 ± 1.0 | 1.9 ± 0.9 | 2.8 ± 1.0 | 1.8 ± 0.5 |
| Texoka | 4.8 ± 1.8 | 3.9 ± 1.5 | 5.6 ± 2.3 | 4.5 ± 1.6 |

[1]The first and second shoots were removed from 10 stolons, and on each shoot the first and second leaves were measured; thus data is an average of 10 measurements.

TABLE 3

Leaf Blade Width Characteristics: University of Nebraska Greenhouse Winter 1988

| | Leaf Blade Width (mm)[1] | | | |
|---|---|---|---|---|
| | Shoot 1 | | Shoot 2 | |
| | Leaf 1 | Leaf 2 | Leaf 1 | Leaf 2 |
| NE 84-315 | 1.2 ± 0.2 | 1.3 ± 0.3 | 1.2 ± 0.2 | 1.2 ± 0.3 |
| 609 | 1.2 ± 0.1 | 1.1 ± 0.5 | — | — |
| Texoka | 1.2 ± 0.2 | 1.3 ± 0.4 | 1.2 ± 0.2 | 1.3 ± 0.4 |

[1]The first and second shoots were removed from 10 stolons, and on each shoot the first and second leaves were measured; thus data is an average of 10 measurements.

TABLE 4

Spikelet Length Characteristics: University of Nebraska John Seaton Anderson Turfgrass Research Facility, Mead, NE Summer 1991

| | Spikelet Length (mm)[1] |
|---|---|
| NE 84-315 | 3.9 ± 1.0 |
| 609 | 3.5 ± 0.7 |
| Texoka | 10.8 ± 2.0 |

[1]Average of 20 measurements.

TABLE 5

Canopy Density and Female Inflorescence Characteristics: July 4, 1989 Buffalograss Trial, Mead, NE (Est. 06/86)

| | Canopy Density[1] | Inflorescence Number | Inflorescence Height (cm) |
|---|---|---|---|
| NE 84-315 | 3.0 a* | 28.5 a | 2.1 a |
| 609 | 1.0 b | 26.5 ab | 4.3 a |
| Texoka | 1.3 b | 15.8 b | 3.5 a |

[1]Canopy Density is rated 1 = open, 2 = average, 3 = closed.

*Means within a column followed by the same letter are not significantly different using Waller-Duncan multiple comparison procedures (K = 100).

TABLE 6

Pubescence Evaluations of Leaf Lamina: University of Nebraska Greenhouse Winter 1993

| | Abaxial Surface | | Adaxial Surface | |
|---|---|---|---|---|
| | Rating[1] | Count[2] | Rating | Count |
| NE 84-315 | 2.4 | 6.5 | 2.8 | 4.9 |
| 609 | 0 | 0 | 0 | 0.1 |
| Prairie | 0 | 0.1 | 0.3 | 0.2 |

[1]Pubescence rating 0–5 scale, 5 = most, average of 8 ratings.
[2]Trichomes per 1 $mm^2$, average of 8 counts, an area 2.45 mm long by the width of the leaf was evaluated on 8 leaves.

TABLE 7

Percent Cover: Buffalograss Regional Trial Dallas, TX[1] (Est. 5/17/88)

| | 6/23/88 | 7/26/88 | 3/25/89 | 4/8/89 |
|---|---|---|---|---|
| NE 84-315 | 7.3 c* | 18.0 c | 60.0 b | 70.0 b |
| 609 | 19.3 ab | 41.3 ab | 87.7 a | 88.3 a |
| Prairie | 21.0 a | 56.7 a | 96.7 a | 100.0 a |
| Texoka | 12.3 bc | 21.0 c | 78.3 ab | 85.0 ab |

*Means within a column followed by the same letter are not significantly different using the Waller-Duncan multiple comparison procedures (K = 100).
[1]Data taken by Dr. B. Ruemmele.

TABLE 8

Establishment Vigor: 1990 Colorado State Buffalograss Trial Fort Collins, CO[1] (Est. 9/89)

| | Establishment Vigor[2] | | % Sprig Survival |
|---|---|---|---|
| | May | July | June 13 |
| NE 84-315 | 2.3[1] | 3.0 | 100 |
| 609 | 2.7 | 3.3 | 92 |
| Prairie | 1.7 | 1.7 | 33 |
| Texoka | 3.0 | 3.7 | 100 |
| LSD (.05) | 0.9 | — | — |

[1]Data taken by Dr. R. Cuany.
[2]1 to 4 scale with 4 = best establishment vigor.

TABLE 9

Establishment Percent Cover, 1990: Southern Illinois Buffalograss Trial Carbondale, Illinois[1] (Est. 5/30/90)

| | 6/12 | 7/17 | 8/15[2] | 9/17 | 10/18 |
|---|---|---|---|---|---|
| NE 84-315 | 25.0 a* | 98.3 a | 83.3 a | 98.7 a | 99.7 a |
| 609 | 25.0 a | 53.3 b | 5.0 b | 33.3 b | 55.0 b |
| Texoka | 20.7 a | 83.3 a | 63.3 a | 86.7 a | 91.7 a |

*Means within a column followed by the same letter are not significantly different using the Waller-Duncan multiple comparison procedures (K = 100).
[1]Data taken by Dr. K. Diesburg.
[2]Herbicide Damage Occurred.

TABLE 10

Stolon Production and Length: 1988 Buffalograss Regional Trial Dallas, TX[1] (Est. 5/17/88)

| | # Stolens | Stolon Length (cm) | | |
|---|---|---|---|---|
| | 49 days | 49 days | 57 days | 70 days |
| NE 84-315 | 8.1 b* | 2.6 b | 3.5 b | 5.1 c |
| 609 | 10.7 ab | 6.1 a | 8.0 a | 10.6 a |
| Prairie | 7.1 a | 5.4 a | 7.5 a | 9.5 ab |
| Texoka | 4.1 b | 2.5 b | 4.9 b | 6.5 c |

*Means within a column followed by the same letter are not significantly different using the Waller-Duncan multiple comparison procedures (K = 100).
[1]Data taken by Dr. B. Ruemmele.

TABLE 11

Establishment Ratings in Three Buffalograss Trials at Mead, NE.

| | Established 7/13/90 | | | | |
|---|---|---|---|---|---|
| | Stolon length (cm) | % Cover | Established 8/8/90 % Cover | Established 5/29/91 % Cover | |
| | 9/6/90 | 6/12/91 | 7/24/91 | 9/26/91 | 6/24/92 |
| NE 84-315 | 19.0 | 27 | 53 | 40 | 50 |
| 609 | 20.7 | 17* | 27* | 33 | 10* |
| Prairie | 52.7 | 27 | 77 | 43 | 17* |
| Texoka | 9.0 | 30 | 37 | 47 | 40 |
| LSD (.05) | 34 | 20 | 27 | 21 | 13 |

*Low % cover due to winter injury.

TABLE 12

Percent Spring Greenup: 1989–91 Buffalograss Clonal Evaluation John Seaton Anderson Facility, Mead, NE (Est. 1986).

| | 5/11/89 | 5/15/91 | Ave |
|---|---|---|---|
| NE 84-315 | 54 | 65 | 60 |
| 609 | 22 | 50 | 36 |
| Texoka | 28 | 48 | 38 |
| LSD (0.5) | 15 | 19 | — |

TABLE 13

Percent Spring Greenup: 1989 Buffalograss Regional Trial Dallas, Texas[1] (Est. 5/17/88)

| | 3/15 | 3/22 | 3/29 | 4/5 | 4/15 |
|---|---|---|---|---|---|
| NE 84-315 | 8.0 b* | 43.3 a | 98.3 a | 99.0 a | 99.0 |
| 609 | 20.0 b | 40.0 a | 83.3 b | 96.3 ab | 99.0 |
| Prairie | 40.0 a | 40.0 a | 73.3 b | 93.3 b | 99.0 |
| Texoka | 20.0 b | 50.0 a | 95.0 a | 97.7 a | 99.0 |

*Means within a column followed by the same letter are not significantly different using the Waller-Duncan multiple comparison procedures (K = 100).
[1]Data taken by B. Ruemmele.

TABLE 14

Percent Fall Dormancy: 1989–91 Buffalograss Clonal Evaluation John Seaton Anderson Facility, Mead, NE. (Est. 1986)

| Experimental | 10/89 | 10/90 | 10/91 | Ave |
|---|---|---|---|---|
| NE 84-315 | 80 | 78 | 75 | 78 |
| 609 | 40 | 28 | 22 | 30 |
| Texoka | 55 | 38 | 35 | 43 |
| LSD (.05) | 18 | 19 | 19 | — |

TABLE 15

Turfgrass Color 1989–90 Buffalograss Regional Trial Dallas, Texas (Est. 5/17/88) Turfgrass Color[2]

| | 1989 | | | | | 1990 | | |
|---|---|---|---|---|---|---|---|---|
| Entry | 20 Jun | 10 Aug | 13 Sep | 21 Sep | 31 Oct | 23 Nov | 04 Jan | 24 Jan |
| NE 84-315 | 7.3 | 8.7 | 1.7 | 2.7 | 1.3 | 1.0 | 1.0 | 1.0 |
| 609 | 6.7 | 7.0 | 7.0 | 7.3 | 7.3 | 7.0 | 2.3 | 1.0 |
| Prairie | 5.0 | 3.7 | 4.3 | 3.3 | 4.3 | 5.0 | 2.3 | 1.0 |
| Texoka | 6.7 | 4.3 | 1.3 | 1.3 | 1.7 | 1.3 | 1.7 | 1.0 |
| C.V. | 21.5 | 16.0 | 25.9 | 31.7 | 24.8 | 30.2 | 22.3 | 0.0 |

[1]Data taken by Dr. B. Ruemmele.
[2]Turfgrass color is rated 1–9, with 1 = brown, 5 = med green, and 9 = dark green.

TABLE 16

Turfgrass Color: 1990 Buffalograss Clonal Evaluation, Mead, Nebraska (Est. 1986)

| | 6/8[1] | 6/15 | 7/30 | 8/10 | 9/13 | AVG |
|---|---|---|---|---|---|---|
| NE 84-315 | 8.0 | 7.3 | 6.8 | 6.3 | 7.3 | 7.1 |
| 609 | 6.0 | 5.8 | 7.3 | 6.8 | 7.3 | 6.6 |
| Texoka | 5.5 | 5.8 | 6.8 | 6.3 | 7.0 | 6.3 |
| LSD (0.05) | 1.2 | 1.4 | 1.1 | 1.2 | 1.1 | – |

[1]Turfgrass color is rated 1–9, with 1 = brown, 5 = med green, and 9 = dark green.

TABLE 17

Turfgrass Quality: 1989 Buffalograss Regional Trial Dallas, Texas[1] (Est. 5/17/88) Turfgrass Quality$_2$

| | 1989 | | | | | |
|---|---|---|---|---|---|---|
| | 08 Apr | 06 May | 27 May | 20 Jun | 10 Aug | 13 Sep |
| NE 84-315 | 6.0[2] | 7.3 | 6.0 | 5.7 | 6.3 | 3.3 |
| 609 | 6.3 | 7.3 | 8.0 | 7.3 | 9.0 | 7.7 |
| Prairie | 6.0 | 7.3 | 7.0 | 8.0 | 7.7 | 7.3 |
| Texoka | 4.7 | 6.0 | 6.3 | 6.0 | 6.3 | 4.0 |
| MSD[3] | 2.4 | n.s.[4] | 1.6 | 1.5 | 1.8 | 0.9 |

| | 1990 | | | | | | |
|---|---|---|---|---|---|---|---|
| | 21 Sep | 31 Oct | 23 Nov | 04 Jan | 24 Jan | 25 Feb | 12 Date Avg |
| NE 84-315 | 3.7 | 3.3 | 3.3 | 3.3 | 3.0 | 3.0 | 4.5 |
| 609 | 8.7 | 9.0 | 8.7 | 7.0 | 6.0 | 5.7 | 7.6 |
| Prairie | 7.7 | 8.3 | 8.3 | 7.0 | 6.0 | 5.7 | 7.2 |
| Texoka | 4.7 | 4.0 | 4.7 | 4.3 | 4.0 | 3.7 | 4.9 |
| MSD[3] | 1.0 | 1.7 | 1.3 | 1.0 | 0.5 | 1.0 | 0.5 |

TABLE 17-continued

Turfgrass Quality: 1989 Buffalograss Regional Trial Dallas, Texas[1] (Est. 5/17/88) Turfgrass Quality$_2$

[1]Data taken by Dr. B. Ruemmele.
[2]Turf quality is rated 1–9, 9 = best.
[3]MSD = Minimum significant Difference to separate classes within each column using the Waller-Duncan K ratio T Test (K ratio = 100).
[4]n.s. indicates dates where no significant differences were determined among the means.

TABLE 18

Turfgrass Quality: 1990 Buffalograss Regional Trial Dallas, Texas[1] (Est. 5/17/88)

| Experimental | 5/29 | 6/24 | 7/29 | 9/24 | 10/31 |
|---|---|---|---|---|---|
| NE 84-315 | 6.8a[4] | 5.4b | 3.5b | 2.9b | 2.3b |
| 609 | 6.9a | 6.9a | 5.7a | 5.2a | 5.1a |
| Texoka | 4.3b | 4.0c | 3.1b | 3.0b | 2.3b |
| Prairie | 6.8a | 6.6a | 6.1a | 4.8a | 4.5a |

| Experimental | 11/15 | 11/25 | 12/20[2] | 12/20[3] |
|---|---|---|---|---|
| NE 84-315 | 2.5b | 2.9b | 2.5b | 3.1cd |
| 609 | 5.0a | 4.5a | 3.9a | 5.1a |
| Texoka | 2.4b | 2.7bc | 2.1c | 3.1cd |
| Prairie | 4.9a | 4.8a | 3.8a | 5.2a |

[1]Data taken by Dr. Ruemmele
Turfgrass Quality is rated 1–9, 9 = best, average of density, uniformity, color and texture.
[2]Includes density for green tissue.
[3]Includes density of all tissue.
[4]Means within a column followed by the same letter are not significantly different using the Waller-Duncan multiple comparison procedures (K = 100).

TABLE 19

Turfgrass Quality: 1989–90 University of Georgia Buffalograss Trial Tifton, GA[1] (Est. 6/9/88)

| | 1989 | | | |
|---|---|---|---|---|
| | 6/14[2] | 7/7 | 9/15 | 10/24 |
| NE 84-315 | — | 3.5 | 6.5 | 7.0 |
| 609 | — | 2.0 | 6.0 | 6.0 |
| Prairie | 3.0 | 2.0 | 6.5 | 6.5 |
| Texoka | 2.0 | 4.5 | 5.5 | 4.5 |
| LSD (.05) | .8 | 1.1 | 1.8 | 1.5 |

| | 1990 | | | | |
|---|---|---|---|---|---|
| | 4/27 | 6/4 | 7/19 | 9/7 | 10.19 |
| NE 84-315 | 7.5 | 8.5 | 8.0 | 6.5 | 7.0 |
| 609 | 7.5 | 7.5 | 7.0 | 6.0 | 6.5 |
| Prairie | 8.0 | 7.0 | 7.5 | 6.5 | 8.0 |
| Texoka | 6.0 | 6.5 | 6.5 | 4.0 | 5.0 |
| LSD (.05) | 0.9 | 1.0 | 1.9 | 1.2 | 1.5 |

[1]Data taken by Dr. W. Hanna.
[2]Turfgrass Quality: 1–9, 9 = best.

TABLE 20

Turfgrass Quality[1]: 1988–91 Buffalograss Clonal

| | 1988 | 1989 | 1990 | 1991 | Ave |
|---|---|---|---|---|---|
| NE 84-315 | 4.8 | 5.3 | 5.6 | 5.2 | 5.2 |
| 609 | 4.8 | 5.0 | 5.0 | 4.4 | 4.8 |
| Texoka | 3.8 | 4.4 | 4.4 | 3.8 | 4.1 |
| LSD (.05) | — | 1.0 | 0.9 | 0.8 | — |

[1]Turfgrass quality is rated 1–9, 9 = best.

TABLE 21

Summer Stress: 1990 Buffalograss Regional Trial Dallas, TX[1] (Est. 9/4/89)

| | June 24[2] | July 6 | July 18 | July 29 |
|---|---|---|---|---|
| NE 84-315 | 6.3 b[3] | 5.7 c | 4.0 c | 3.0 c |
| 609 | 8.0 a | 8.0 a | 7.0 a | 6.7 a |
| Prairie | 8.0 a | 8.0 a | 7.3 a | 6.3 a |
| Texoka | 6.3 b | 6.7 b | 5.3 b | 5.0 b |

[1]Data taken by Dr. Ruemmele.
[2]Summer Stress is rated 9 to 1 with 9 = no sign of drought or heat stress and 1 = dormant.
[3]Means within a column followed by the same letter are not significantly different using the Waller-Duncan multiple comparison procedures (K = 100).

TABLE 22

Frost Tolerance: Buffalograss Regional Trial, Dallas, Texas*

| | Frost Damage[1] |
|---|---|
| NE 84-315 | 7.0 a[2] |
| 609 | 7.0 a |
| Texoka | 3.0 c |
| Prairie | 7.0 a |

TABLE 22-continued

Frost Tolerance: Buffalograss Regional Trial, Dallas, Texas*

| | Frost Damage[1] |
|---|---|

*Data taken by Dr. Ruemmele.
[1]Frost damage is rated 1–9, 9 = no damage.
[2]Means within a column followed by the same letter are not significantly different using the Waller-Duncan comparison procedures (K = 100).

TABLE 23

Turfgrass Density: 1990 Buffalograss Clonal Evaluation, Mead, NE (Est. 1986)

| | 6/8[1] | 6/15 | 7/30 | 8/10 | 9/13 | AVG |
|---|---|---|---|---|---|---|
| NE 84-315 | 5.8 | 7.3 | 5.8 | 5.3 | 4.8 | 5.8 |
| 609 | 2.5 | 3.8 | 4.3 | 6.3 | 6.8 | 4.7 |
| Texoka | 3.0 | 3.0 | 3.5 | 4.8 | 4.8 | 3.8 |
| LSD (0.05) | 1.3 | 1.9 | 1.2 | 1.2 | 1.7 | — |

[1]Turfgrass Density is rated 1–9, 9 = most dense.

TABLE 24

Plant Height (cm): 1990 Buffalograss Clonal Evaluation John Seaton Anderson Facility, Mead, Nebraska (Est. 1986)

| | |
|---|---|
| NE 84-315 | 5.8 |
| 609 | 6.3 |
| Texoka | 7.6 |
| LSD (.05) | 1.1 |

#7bB:Pat315

We claim:

1. A new and distinct perennial female buffalograss plant substantially distinguished by its heat, drought and cold tolerance, excellent dark green color, high density, wear tolerance, low maintenance requirements and slow rate of establishment as herein shown and described.

* * * * *